(12) United States Patent
Kimura et al.

(10) Patent No.: US 8,900,785 B2
(45) Date of Patent: Dec. 2, 2014

(54) CHARGE CONTROL AGENT AND TONER USING THE SAME

(75) Inventors: Ikuo Kimura, Ibaraki (JP); Masami Ito, Ibaraki (JP); Masaya Tojou, Ibaraki (JP); Kanae Hiraishi, Ibaraki (JP); Masafumi Asakai, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/819,178

(22) PCT Filed: Sep. 2, 2011

(86) PCT No.: PCT/JP2011/070019
§ 371 (c)(1),
(2), (4) Date: Feb. 26, 2013

(87) PCT Pub. No.: WO2012/035996
PCT Pub. Date: Mar. 22, 2012

(65) Prior Publication Data
US 2013/0157190 A1    Jun. 20, 2013

(30) Foreign Application Priority Data
Sep. 14, 2010    (JP) ................. 2010-205013

(51) Int. Cl.
*G03G 9/08*    (2006.01)
*G03G 9/097*    (2006.01)
(Continued)

(52) U.S. Cl.
CPC ........ *G03G 9/09766* (2013.01); *G03G 9/09733* (2013.01); *C07D 403/06* (2013.01);
(Continued)

(58) Field of Classification Search
CPC ................. G03G 9/09758; G03G 9/09775
USPC ................. 430/108.21; 544/302, 306
See application file for complete search history.

(56) References Cited

U.S. PATENT DOCUMENTS 4,206,064 A    6/1980    Kiuchi et al.
(Continued)

FOREIGN PATENT DOCUMENTS

EP    0 242 420    10/1987
JP    55-042752    11/1980
(Continued)

OTHER PUBLICATIONS

U.S. Appl. No. 13/817,937 to Ikuo Kimura et al., filed Feb. 20, 2013.
(Continued)

*Primary Examiner* — Mark A Chapman
(74) *Attorney, Agent, or Firm* — Greenblum & Bernstein, P.L.C.

(57) ABSTRACT

A charge control agent comprises a barbituric acid derivative represented by the following general formula (1):

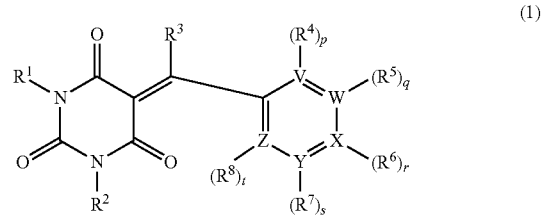

wherein $R^1$ to $R^8$ are alkyl groups, cycloalkyl groups or aryl groups,
V, W, X, Y and Z are carbon atoms or nitrogen atoms, at least two of which being carbon atoms, and
p, q, r, s and t are the numbers of 0 or 1.

7 Claims, 1 Drawing Sheet

(51) Int. Cl.
*C07D 403/06* (2006.01)
*C07D 239/60* (2006.01)
*C07D 401/10* (2006.01)
*C07D 239/62* (2006.01)
*C07D 401/06* (2006.01)
*C07D 401/14* (2006.01)

(52) U.S. Cl.
CPC ........ *G03G 9/09741* (2013.01); *G03G 9/09758* (2013.01); *C07D 239/60* (2013.01); *G03G 9/09775* (2013.01); *C07D 401/10* (2013.01); *C07D 239/62* (2013.01); *G03G 9/0975* (2013.01); *C07D 401/06* (2013.01); *C07D 401/14* (2013.01)
USPC ........................ 430/108.21; 544/302; 544/306

(56) References Cited

U.S. PATENT DOCUMENTS

| | | | |
|---|---|---|---|
| 4,338,390 A | 7/1982 | Lu | |
| 4,391,890 A | 7/1983 | Lu | |
| 4,394,430 A | 7/1983 | Jadwin et al. | |
| 4,396,697 A | 8/1983 | Ciccarelli et al. | |
| 4,403,027 A | 9/1983 | Ishikawa et al. | |
| 4,656,112 A | 4/1987 | Kawagishi et al. | |
| 4,673,631 A | 6/1987 | Kufumoto et al. | |
| 4,767,688 A | 8/1988 | Hashimoto et al. | |
| RE32,883 E | 3/1989 | Lu | |
| 5,049,467 A | 9/1991 | Yamanaka | |
| 5,100,928 A * | 3/1992 | Grosso et al. | 522/25 |
| 5,952,145 A | 9/1999 | Yamanaka et al. | |
| 7,709,172 B2 | 5/2010 | Yasumura et al. | |
| 7,820,832 B2 | 10/2010 | Yasumura et al. | |
| 7,901,858 B2 | 3/2011 | Yasumura et al. | |
| 2009/0104554 A1 | 4/2009 | Otsuka et al. | |
| 2012/0315573 A1 | 12/2012 | Otsuka et al. | |

FOREIGN PATENT DOCUMENTS

| | | |
|---|---|---|
| JP | 57-111541 | 7/1982 |
| JP | 57-119364 | 7/1982 |
| JP | 58-009154 | 1/1983 |
| JP | 58-098742 | 6/1983 |
| JP | 61-003149 | 1/1986 |
| JP | 61-069073 | 4/1986 |
| JP | 61-141453 | 6/1986 |
| JP | 61-221756 | 10/1986 |
| JP | 62-094856 | 5/1987 |
| JP | 1-306861 | 12/1989 |
| JP | 2568675 | 10/1996 |
| JP | 9-171270 | 6/1997 |
| JP | 10-161350 | 6/1998 |
| JP | 2899038 | 3/1999 |
| JP | 3313871 | 5/2002 |
| JP | 2002-179959 | 6/2002 |
| JP | 3325730 | 7/2002 |
| JP | 3359657 | 10/2002 |
| JP | 2003-162100 | 6/2003 |
| JP | 2003-295522 | 10/2003 |
| WO | 2007/111346 | 10/2007 |
| WO | 2007/119797 | 10/2007 |

OTHER PUBLICATIONS

Search report from International Application No. PCT/JP2011/070019, mail date is Oct. 25, 2011.

* cited by examiner

CHARGE CONTROL AGENT AND TONER USING THE SAME

TECHNICAL FIELD

This invention relates to a charge control agent used for an image-forming apparatus for developing electrostatic latent images in the field of electrophotography and electrostatic recording, and to a negatively charging toner containing the charge control agent.

BACKGROUND ART

The image-forming processing based the electrophotographic system forms images by using an inorganic photosensitive material such as selenium, selenium alloy, cadmium sulfide or amorphous silicon or by using an organic photosensitive material formed by using a charge-generating agent and a charge-transporting agent.

Namely, the photosensitive material is positively or negatively charged depending upon the charging characteristic of the photosensitive material and is, thereafter, exposed to image-bearing light. The electrostatic latent image formed by the exposure to image-bearing light is developed by using a toner to form a toner image which is then transferred onto a paper or a plastic film and is fixed to obtain a visible image.

When a charge image (portion irradiated with light) formed by the exposure to image-bearing light is to be developed into a visible image, use is made of a toner which is electrically charged to a polarity opposite to the charged polarity of the photosensitive material. This developing system is called normal development. When a portion (portion irradiated with light) from which the electric charge is removed by the exposure to image-bearing light is to be developed into a visible image, use is made of a toner which is electrically charged to the same polarity as the charged polarity of the photosensitive material. This developing system is called reversal development.

The toner is constituted by dispersing a coloring agent and other additives in a binder resin. As an additive for the toner, there has been known a charge control agent that is used for improving charging properties (rate of charge, charge level, charge stability, etc.).

As the charge control agent used for imparting frictional positively charging property to the toner, there have been known Nigrosine dye, azine dye, copper phthalocyanine pigment, quaternary ammonium salt and a polymer having a quaternary ammonium salt on the side change thereof. Further, as the charge control agent used for imparting frictional negatively charging property to the toner, there have been known a metal complex of monoazo dye, metal complexes of salicylic acid, naphthoic acid and dicarboxylic acid, copper phthalocyanine pigment, and resin containing acid components.

For the colored toners of which the market is expected to expand in the future, it is essential to use a light-colored or, desirably, colorless charge control agent that does not affect the hue. As the light-colored or colorless charge control agent, there can be exemplified metal complex compounds of hydroxybenzoic acid derivatives (e.g., see patent documents 1 to 3), aromatic metal dicarboxylate compounds (e.g., see patent document 4), metal complex compounds of anthranilic acid derivatives (e.g., see patent documents 5 and 6), organoboron compounds (e.g., see patent documents 7 and 8), biphenol compounds (e.g., see patent document 9), calix(n) arene compounds (e.g., see patent documents 10 to 15), and cyclic phenol sulfides (e.g., see patent documents 16 to 18), which are for use with the negatively charging toners. For use with the positively charging toners, there can be exemplified quaternary ammonium salt compounds (e.g., see patent documents 19 to 21).

PRIOR ART DOCUMENTS

Patent Documents

Patent document 1: JP-B-55-042752
Patent document 2: JP-A-61-069073
Patent document 3: JP-A-61-221756
Patent document 4: JP-A-57-111541
Patent document 5: JP-A-61-141453
Patent document 6: JP-A-62-094856
Patent document 7: U.S. Pat. No. 4,767,688
Patent document 8: JP-A-1-306861
Patent document 9: JP-A-61-003149
Patent document 10: Japanese Pat. No. 2568675
Patent document 11: Japanese Pat. No. 2899038
Patent document 12: Japanese Pat. No. 3359657
Patent document 13: Japanese Pat. No. 3313871
Patent document 14: Japanese Pat. No. 3325730
Patent document 15: JP-A-2003-162100
Patent document 16: JP-A-2003-295522
Patent document 17: WO2007-111346
Patent document 18: WO2007-119797
Patent document 19: JP-A-57-119364
Patent document 20: JP-A-58-009154
Patent document 21: JP-A-58-098742

OUTLINE OF THE INVENTION

Problems that the Invention is to Solve

Many of the conventional charge control agents, however, are complexes or salts of heavy metals such as chromium or the like posing problems under the Regulations of Waste Disposal, and are not necessarily safe. Besides, some of them are not completely colorless or are not capable of imparting electric charge to a degree that is required nowadays. Therefore, despite the charge control agent is added, the toner cannot be electrically charged at a sufficiently high rate causing such problems that the initial image lacks vividness and that the quality of image tends to fluctuate when the images are continuously formed. Besides, the charging characteristics of the toner vary to a large extent depending upon the environmental conditions such as temperature, humidity and the like, and the image quality varies conspicuously depending upon a change in the environmental conditions.

As the toners, further, there have been known pulverized toners and polymerized toners. For the polymerized toners, a binder resin is formed by adding additives such as coloring agent and charge control agent to a monomer and conducting the suspension polymerization or the emulsion polymerization. Therefore, the polymerized toners feature nearly constant particle sizes and shapes, a high fluidity and a uniformly charging property. However, the conventional charge control agents are susceptible to the effect of environment. When used for the polymerized toners, therefore, the conventional charge control agent cannot impart electric charge to a satisfactory degree. Accordingly, it has been desired to provide a charge control agent that is capable of imparting an electric charge to a high degree even when it is used for the polymerized toners.

It is, therefore, an object of the present invention is to provide a charge control agent which contains no heavy metal component, does not adversely affect the environment and, besides, is colorless or is light-colored so as to be applied to colored toners, is little affected by the environmental conditions, and exhibits the effect of imparting highly charging power (charge rising property, charge level, charge stability) even when it is used for the polymerized toners.

Another object of the invention is to provide a toner blended with the above charge control agent.

Means for Solving the Problems

According to the present invention, there is provided a charge control agent comprising a barbituric acid derivative represented by the following general formula (1).
General formula (1):

[Chemical 1]

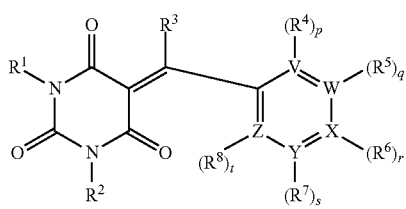
(1)

wherein, $R^1$ and $R^2$ may be the same or different, and are alkyl groups having 1 to 6 carbon atoms, cycloalkyl groups having 5 to 8 carbon atoms, aryl groups or heterocyclic groups, $R^3$ is a hydrogen atom, an alkyl group having 1 to 8 carbon atoms, a cycloalkyl group having 5 to 10 carbon atoms, an alkenyl group having 2 to 6 carbon atoms, an alkyloxy group having 1 to 8 carbon atoms, a cycloalkyloxy group having 5 to 10 carbon atoms, an aryloxy group, an aryl group or a hetrocyclic group, $R^4$ to $R^8$ may be the same or different, and are hydrogen atoms, deuterium atoms, fluorine atoms, chlorine atoms, bromine atoms, iodine atoms, hydroxyl groups, cyano groups, nitro groups, alkyl groups having 1 to 8 carbon atoms, cycloalkyl groups having 5 to 10 carbon atoms, alkenyl groups having 2 to 6 carbon atoms, alkyloxy groups having 1 to 8 carbon atoms, cycloalkyloxy groups having 5 to 10 carbon atoms, aryl groups, heterocyclic groups or aryloxy groups, and may be bonded to each other to form a ring and, further, $R^4$ may be bonded to $R^3$ to form a ring, V, W, X, Y and Z are carbon atoms or nitrogen atoms, and at least two of V, W, X, Y and Z are carbon atoms, p is a number of 0 or 1, and is 1 if V is a carbon atom and is 0 if V is a nitrogen atom, q is a number of 0 or 1, and is 1 if W is a carbon atom and is 0 if W is a nitrogen atom, r is a number of 0 or 1, and is 1 if X is a carbon atom and is 0 if X is a nitrogen atom, s is a number of 0 or 1, and is 1 if Y is a carbon atom and is 0 if Y is a nitrogen atom, and t is a number of 0 or 1, and is 1 if Z is a carbon atom and is 0 if Z is a nitrogen atom.

In the charge control agent of the present invention, it is desired that:

(1) In the above general formula (1), $R^1$ and $R^2$ are alkyl groups having 1 to 4 carbon atoms but without substituent, cycloalkyl groups having 5 to 6 carbon atoms but without substituent, or substituted or unsubstituted aryl groups;

(2) In the above general formula (1), $R^3$ is a hydrogen atom; and (3) In the above general formula (1), V, W, X, Y and Z are all carbon atoms.

According to the present invention, further, there is provided a toner containing the above-mentioned charge control agent, a coloring agent and a binder resin.

In the above toner, it is desired that:

(4) The charge control agent is dispersed in the binder resin in an amount of 0.1 to 10 parts by mass per 100 parts by mass of the binder resin, and the coloring agent is dispersed in the binder resin in an amount of 0.1 to 20 parts by mass per 100 parts by mass of the binder resin.

Further, the toner may be the one that is obtained by either a pulverization method or a polymerization method.

Effects of the Invention

The barbituric acid derivative represented by the above general formula (1) is a compound that contains no heavy metal component such as chromium that adversely affects the environment, and remains very stable and favorably disperses in a resin. Therefore, the charge control agent of the invention comprising the barbituric acid derivative is highly safe, does not adversely affect the environment even after it is disposed of as a waste matter, is not affected by the environmental conditions, is capable of imparting stable and excellent charging power (negatively charging power) to the toner and, specifically, exhibits the effect of imparting excellent charging power when it is used not only for the pulverized toner but also for the polymerized toner. Besides, the charge control agent (barbituric acid derivative) is of a colorless or light-colored crystalline form and does not impair the hue of the colored toner even when it is used for the colored toner.

The toner blended with the charge control agent is quickly and negatively charged when it is rubbed, features a quick rise of charging, holds a large amount of electric charge over an extended period of time maintaining stability despite the environmental conditions are varied, and makes it possible to obtain an image free of fogging and having good image density, dot reproducibility and fine line reproducibility.

MODE FOR CARRYING OUT THE INVENTION

Figure 1:
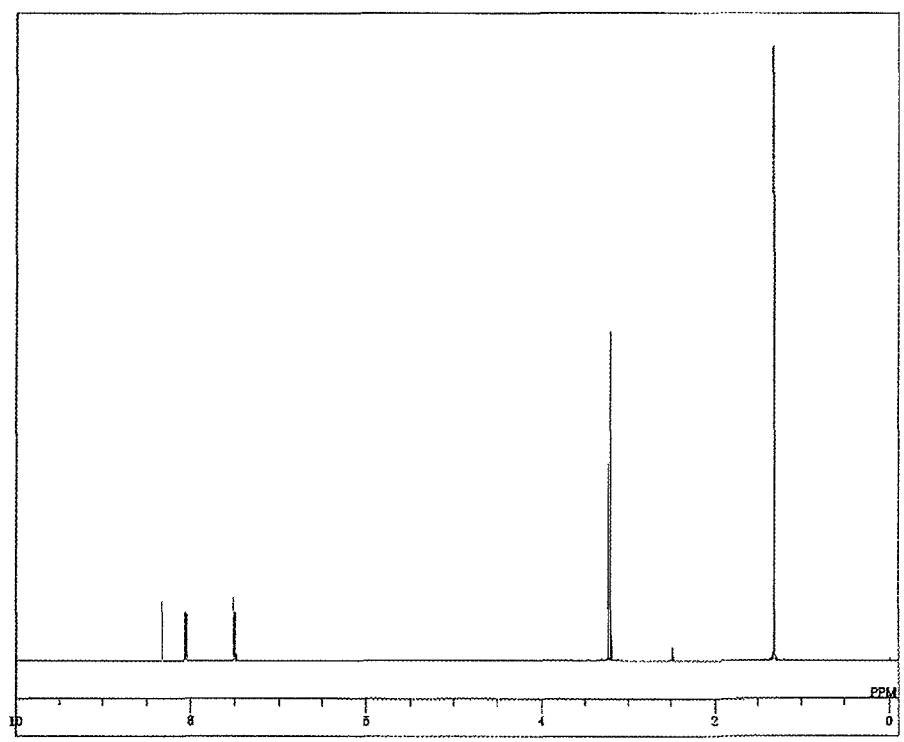
FIG. 1 is a 1H-NMR chart of a compound (Example compound No. 1) according to Example 1 of the present invention.

The charge control agent of the present invention comprises a barbituric acid derivative represented by the following general formula (1).

[Chemical 2]

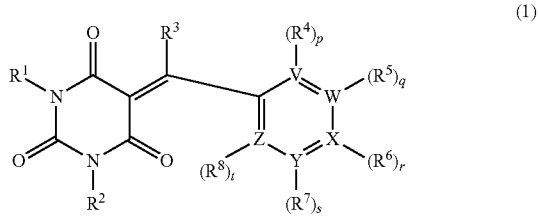
(1)

The above barbituric acid derivative can be produced by a known method. For example, a 1,3-di-substituted barbituric acid that corresponds to the above general formula (1) is condensed with an aldehyde or a ketone to synthesize the barbituric acid derivative which is a charge control agent of the present invention.

<$R^1, R^2$>

In the above general formula (1), $R^1$ and $R^2$ may be the same or different, and are alkyl groups having 1 to 6 carbon atoms, cycloalkyl groups having 5 to 8 carbon atoms, aryl groups or heterocyclic groups. There groups may or may not have a substituent.

The numbers of carbon atoms in the above alkyl group and cycloalkyl group do not include the number of carbon atoms possessed by the substituent.

The above alkyl group may be in the form of either a straight chain or a branch so far as the number of carbon atoms are within the above range. As the alkyl group, there can be exemplified methyl group, ethyl group, n-propyl group, isopropyl group, n-butyl group, isobutyl group, tert-butyl group, n-pentyl group, isopentyl group, neopentyl group and n-hexyl group.

Further, as the cycloalkyl group, there can be exemplified cyclopentyl group and cyclohexyl group.

As the aryl group, there can be exemplified phenyl group, biphenylyl group, terphenylyl group, naphthyl group, anthracenyl group, phenanthryl group, fluorenyl group, indenyl group, pyrenyl group, perylenyl group, fluoranthenyl group and triphenylenyl group.

As the heterocyclic group, there can be exemplified pyridyl group, furanyl group, pyranyl group, thienyl group, furyl group, pyrrolyl group, thiophenyl group, pyrrolidinyl group, imidazolyl group, imidazolinyl group, imidazolidinyl group, pyrazolyl group, pyrazolinyl group, pyrazolidinyl group, pyridazinyl group, pyradinyl group, piperidinyl group, piperadinyl group, thioranyl group, thianyl group, quinolyl group, isoquinolyl group, benzofuranyl group, benzothiophenyl group, indolyl group, carbazolyl group, benzoxazolyl group, benzothiazolyl group, quinoxalyl group, benzoimidazolyl group, pyrazolyl group, dibenzofuranyl group, dibenzothiophenyl group and carbolinyl group.

As the substituent which may be possessed by the above-mentioned groups $R^1$ and $R^2$, there can be exemplified the following groups.

Deuterium atom;

Alkyl group with C number of 1 to 8, such as methyl group, ethyl group, n-propyl group, isopropyl group, n-butyl group, isobutyl group, tert-butyl group, n-pentyl group, isopentyl group, neopentyl group, n-hexyl group, n-heptyl group, isoheptyl group, n-octyl group and isooctyl group;

Trifluoromethyl group;

Cyano group;

Nitro group;

Halogen atom such as fluorine atom, chlorine atom, bromine atom, and iodine atom;

Alkoxy group with C number of 1 to 8, such as methoxy group, ethoxy group and propyloxy group;

Alkenyl group with C number of 2 to 6, such as vinyl group, allyl group, 2-butenyl group and 1-hexenyl group;

Aralkyl group such as benzyl group, naphthylmethyl group and phenetyl group;

Aryloxy group such as phenoxy group and tolyloxy group;
Arylalkoxy group such as benzyloxy group and phenetyloxy group;

Aryl group such as phenyl group, biphenylyl group, terphenylyl group, naphthyl group, anthracenyl group, phenanthryl group, fluorenyl group, indenyl group, pyrenyl group, perylenyl group, fluoranthenyl group and triphenylenyl group;

Heterocyclic group such as pyridyl group, furanyl group, pyranyl group, thienyl group, furyl group, pyrrolyl group, thiophenyl group, pyrrolidinyl group, imidazolyl group, imidazolinyl group, imidazolidinyl group, pyrazolyl group, pyrazolinyl group, pyrazolidinyl group, pyridazinyl group, pyradinyl group, piperidinyl group, piperadinyl group, thioranyl group, thianyl group, quinolyl group, isoquinolyl group, benzofuranyl group, benzothiophenyl group, indolyl group, carbazolyl group, benzoxazolyl group, benzothiazolyl group, quinoxalyl group, benzoimidazolyl group, pyrazolyl group, dibenzofuranyl group, dibenzothiophenyl group and carbolinyl group;

Arylvinyl group such as styryl group and naphthylvinyl group;

Acyl group such as acetyl group and benzoyl group;

Dialkylamino group such as dimethylamino group and diethylamino group;

Diarylamino group such as diphenylamino group and dinaphthylamino group;

Diaralkylamino group such as dibenzylamino group and diphenetylamino group;

Diheteroamino group such as dipyridylamino group, dithienylamino group and dipiperidinylamino group; and Dialkenylamino group such as diallylamino group.

The substituents exemplified above may further be substituted with a further substituent, and a plurality of substituents may be simply bonded together or may be bonded together via an oxygen atom or a sulfur atom to form a ring.

As the cycloalkyl group, there can be further exemplified cyclopentyl group and cyclohexyl group.

Further, as the substituent which may be possessed by the cycloalkyl group, there can be exemplified alkyl group having 1 to 8 carbon atoms, such as methyl group, ethyl group, n-propyl group, isopropyl group, n-butyl group, isobutyl group, tert-butyl group, n-pentyl group, isopentyl group, neopentyl group, n-hexyl group, n-heptyl group, isoheptyl group, n-octyl group and isooctyl group in addition to the substituents exemplified for the alkyl group.

In the invention, the above-mentioned groups $R^1$ and $R^2$ are preferably alkyl groups with C number of 1 to 4 but without substituent, cycloalkyl groups with C number of 5 or 6 but without substituent, or aryl groups which may have a substituent.

<$R^3$>

In the general formula (1), $R^3$ is a hydrogen atom, an alkyl group having 1 to 8 carbon atoms, a cycloalkyl group having 5 to 10 carbon atoms, an alkenyl group having 2 to 6 carbon atoms, an alkyloxy group (alkoxy group) having 1 to 8 carbon atoms, a cycloalkyloxy group having 5 to 10 carbon atoms, an aryloxy group, an aryl group or a heterocyclic group. These groups may or may not have a substituent. The above numbers of carbon atoms do not include the number of carbon atoms possessed by the substituent.

Here, the group $R^3$ may be bonded to a group $R^4$ that will be described later to form a ring.

As the alkyl group, there can be exemplified n-heptyl group, isoheptyl group, n-octyl group and isooctyl group in addition to the alkyl group exemplified for $R^1$ and $R^2$.

As the cycloalkyl group, there can be exemplified 1-adamantyl group and 2-adamantyl group in addition to the cycloalkyl group exemplified for $R^1$ and $R^2$.

As the alkenyl group, there can be exemplified vinyl group, allyl group, isopropenyl group and 2-butenyl group.

As the alkyloxy group, there can be exemplified methyloxy group, ethyloxy group, n-propyloxy group, isopropyloxy group, n-butyloxy group, tert-butyloxy group, n-pentyloxy group, n-hexyloxy group, n-heptyiloxy group, isoheptyloxy group, n-octyloxy group and isooctyloxy group.

As the cycloalkyloxy group, there can be exemplified cyclopentyloxy group, cyclohexyloxy group, cycloheptyloxy group, cyclooctyloxy group, 1-adamantyloxy group and 2-adamantyloxy group.

As the aryloxy group, there can be exemplified phenoxy group, tolyloxy group, biphenylyloxy group, terphenylyloxy group, naphthyloxy group, anthryloxy group, phenanthryloxy group, fluorenyloxy group, indenyloxy group, pyrenyloxy group and perylenyloxy group.

As the aryl group and the heterocyclic group, there can be exemplified the same groups as those exemplified for $R^1$ and $R^2$.

As the substituent which may be possessed by the above-mentioned groups, there can be exemplified the same substituents as those which may be possessed by $R^1$ and $R^2$. Further, the substituent which may be possessed by the group $R^3$ may, further, possess any other substituent like the case of $R^1$ and $R^2$. Moreover, a plurality of substituents may be simply coupled together or may be coupled together via an oxygen atom or a sulfur atom to form a ring.

In the invention, the above $R^3$ is, preferably, a hydrogen atom.

<$R^4$ to $R^8$>

In the general formula (1), $R^4$ to $R^8$ may be the same or different, and are hydrogen atoms, deuterium atoms, fluorine atoms, chlorine atoms, bromine atoms, iodine atoms, hydroxyl groups, cyano groups, nitro groups, alkyl groups having 1 to 8 carbon atoms, cycloalkyl groups having 5 to 10 carbon atoms, alkenyl groups having 2 to 6 carbon atoms, alkyloxy groups having 1 to 8 carbon atoms, cycloalkyloxy groups having 5 to 10 carbon atoms, aryl groups, heterocyclic groups or aryloxy groups. These groups may or may not have a substituent. The above numbers of carbon atoms do not include the number of carbon atoms possessed by the substituent.

Further, $R^4$ to $R^8$ may be bonded to each other to form a ring and, further, $R^4$ may be bonded to the above $R^3$ to form a ring.

Concrete examples of the alkyl group may be the same groups as those exemplified for the group $R^3$. Among such alkyl groups, a preferred example is an alkyl group (methyl group or ethyl group) with a C number of 1 or 2 and having a substituent that will be described later. It is also preferred to use an alkyl group with a C number of 3 to 8 and having or without having a substituent.

Examples of the cycloalkyl group may be the same groups as those exemplified for the group $R^3$. The cycloalkyl group, too, may or may not have a substituent.

Examples of the alkenyl group may be the same groups as those exemplified for the groups $R^1$ and $R^2$. Among such alkenyl groups, a preferred alkenyl group (vinyl group) has a C number of 2 and a substituent that will be described later. It is also preferred to use an alkenyl group with a C number of 3 to 6 and having or without having a substituent.

As the alkyloxy group, cycloalkyloxy group, aryl group, heterocyclic group and aryloxy group, there can be exemplified the same groups as those exemplified for the group $R^3$. These groups, too, may or may not have a substituent.

As the substituent which may be possessed by the above-mentioned groups, there can be exemplified quite the same substituents as those which may be possessed by $R^1$ and $R^2$. The substituents which may be possessed by the groups $R^4$ to $R^8$ may further possess any other substituent like the case of $R^1$ and $R^2$. Moreover, a plurality of substituents may be simply bonded together or may be bonded together via an oxygen atom or a sulfur atom to form a ring.

Further, the group $R^4$ may be bonded to the above group $R^3$ to form a ring.

Of the above groups $R^4$ to $R^8$, preferred are hydrogen atoms, deuterium atoms, chlorine atoms, cyano groups, nitro groups, alkyl groups with a C number of 1 to 8, alkenyl groups with a C number of 2 to 6, and alkyloxy groups with a C number of 1 to 8. The alkyl groups, alkenyl groups and alkyloxy groups may all have a substituent and may assume the form of either a straight chain or a branch.

In the invention, the most preferred groups $R^4$ to $R^8$ are hydrogen atoms, chlorine atoms, alkyl groups with a C number of 1 to 4 but without having substituent, trifluoromethyl groups, alkenyl groups with a C number of 2 to 4 but without having substituent, and alkyloxy groups with a C number of 1 to 4 but without having substituent. These alkyl groups, alkenyl groups and alkyloxy groups may all assume the form of either a straight chain or a branch.

<V to Z and p to t>

In the general formula (1), V, W, X, Y and Z are carbon atoms or nitrogen atoms. Here, at least two, preferably, four or more and, most preferably, all of V to Z are carbon atoms.

Further, p, q, r, s and t are the numbers of the groups $R^4$ to $R^8$ bonded to V to Z, and are 0 or 1.

Namely, as will be understood from the general formula (1), if any one of V to Z is a nitrogen atom, then none of the groups $R^4$ to $R^8$ are bonded to the nitrogen atom, and p, q, r, s or t representing the number thereof becomes zero. If any one of V to Z is a carbon atom, then any one of $R^4$ to $R^8$ is bonded to the carbon atom, and p, q, r, s or t representing the number thereof becomes 1.

<Preferred Examples of the Barbituric Acid Derivative>

In the invention, preferred examples of the barbituric acid derivative represented by the above general formula (1) are as follows:

[Chemical 3]

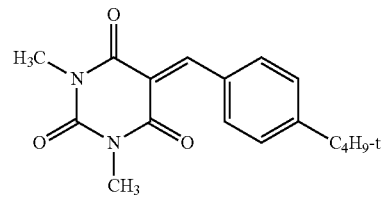

(Example compound 1)

[Chemical 4]

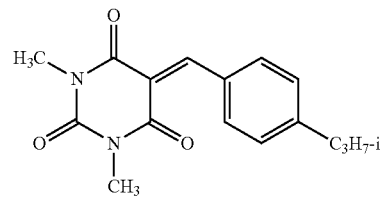

(Example compound 2)

[Chemical 5]

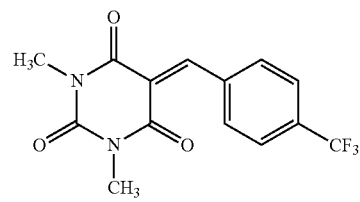

(Example compound 3)

-continued
[Chemical 6]
(Example compound 4)
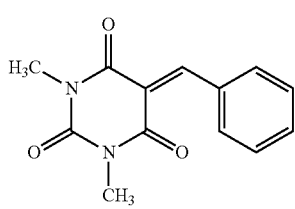
[Chemical 7]
(Example compound 5)
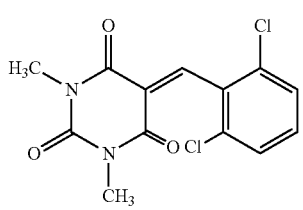
[Chemical 8]
(Example compound 6)
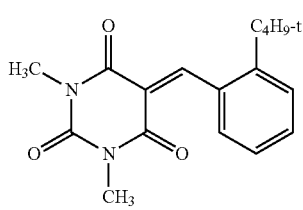
[Chemical 9]
(Example compound 7)
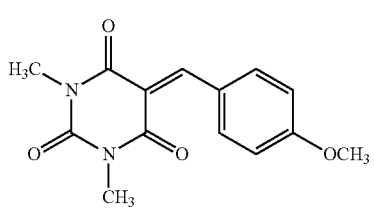
[Chemical 10]
(Example compound 8)
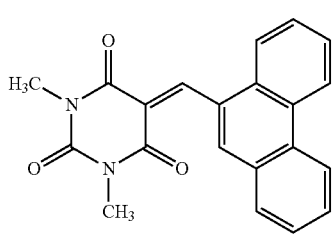
[Chemical 11]
(Example compound 9)
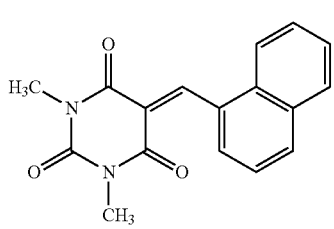
-continued
[Chemical 12]
(Example compound 10)
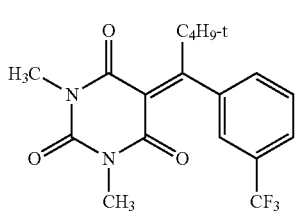
[Chemical 13]
(Example compound 11)
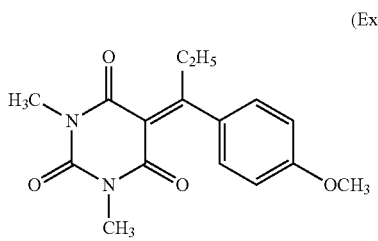
[Chemical 14]
(Example compound 12)
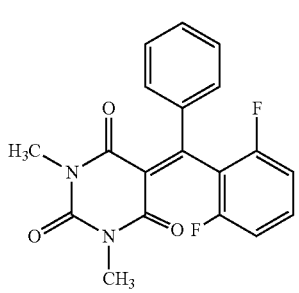
[Chemical 15]
(Example compound 13)
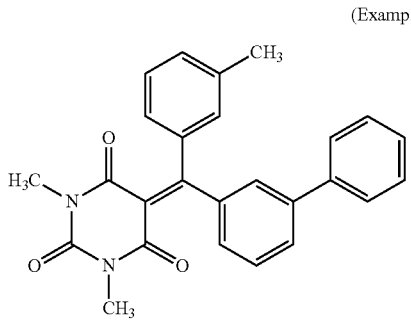
[Chemical 16]
(Example compound 14)
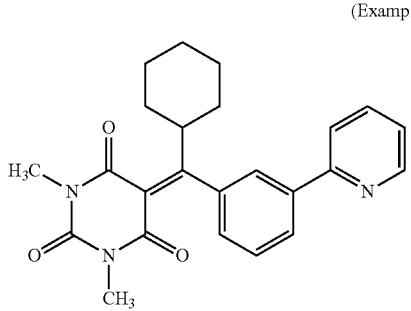

[Chemical 17]
(Example compound 15)
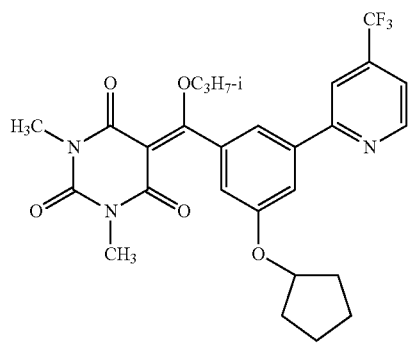
[Chemical 18]
(Example compound 16)
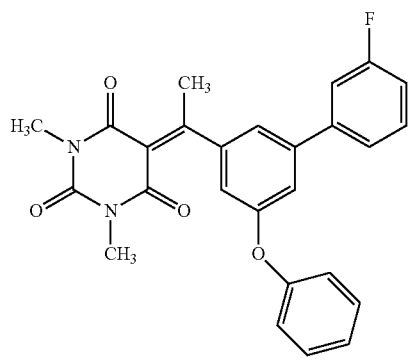
[Chemical 19]
(Example compound 17)
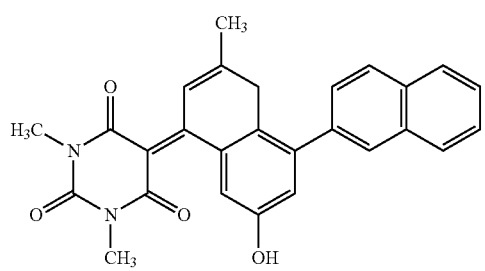
[Chemical 20]
(Example compound 18)
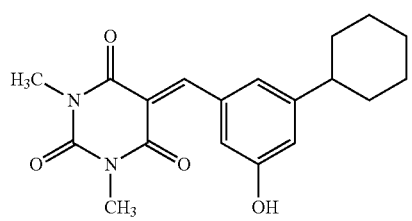
[Chemical 21]
(Example compound 19)
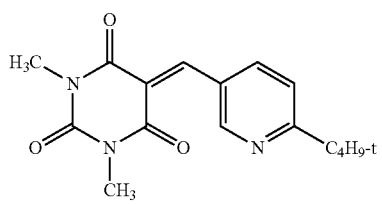
[Chemical 22]
(Example compound 20)
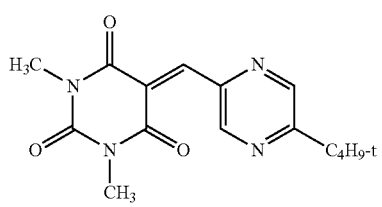
[Chemical 23]
(Example compound 21)
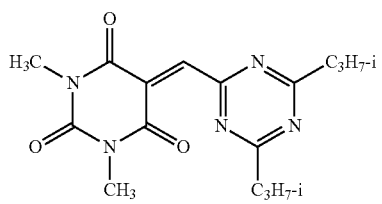
[Chemical 24]
(Example compound 22)
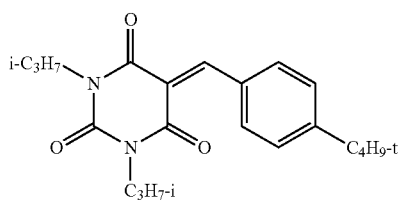
[Chemical 25]
(Example compound 23)
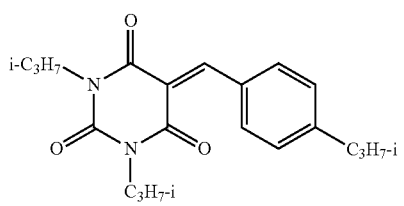

[Chemical 26]

(Example compound 24)

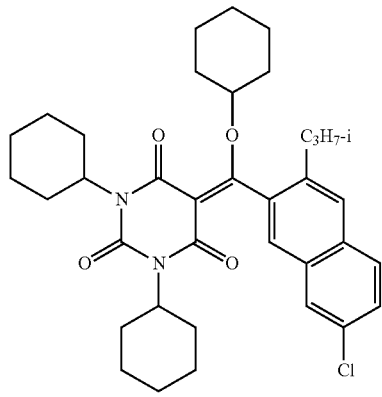

[Chemical 27]

(Example compound 25)

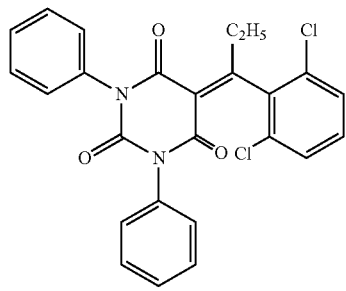

[Chemical 28]

(Example compound 26)

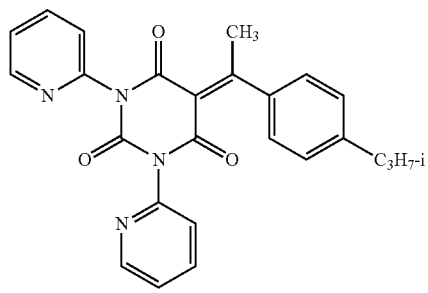

[Chemical 29]

(Example compound 27)

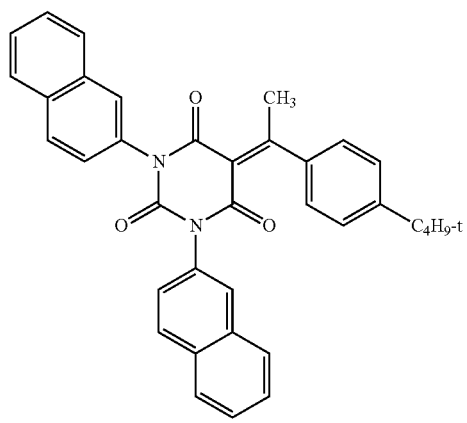

[Chemical 30]

(Example compound 28)

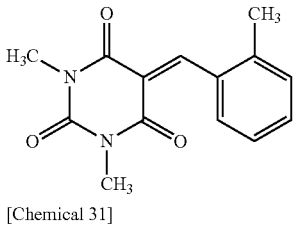

[Chemical 31]

(Example compound 29)

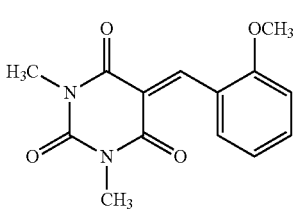

[Chemical 32]

(Example compound 30)

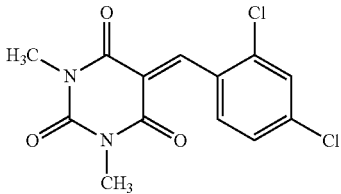

[Chemical 33]

(Example compound 31)

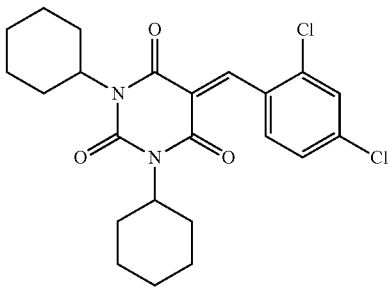

[Chemical 34]

(Example compound 32)

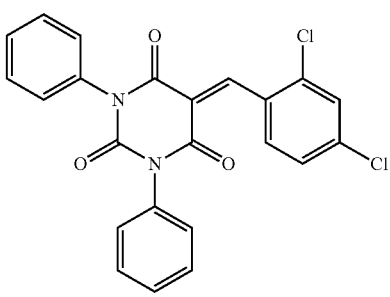

<Charge Control Agent>

In the invention, the barbituric acid derivatives represented by the above general formula (1) are added in one kind or in a combination of two or more kinds to the toner for electrophotography to work as a charge control agent that negatively charges upon friction thereby to improve the negatively charging property of the toner upon friction.

The charge control agent can be used as an external additive so as to mechanochemically adhere onto the surfaces of the toner particles. Usually, however, it is desired that the charge control agent is dispersed as an internal additive in the binder resin of the toner to stably improve the charging property of the toner upon friction.

When used as the external additive, the charge control agent is used in an amount of 0.01 to 5 parts by mass and, specifically, 0.01 to 2 parts by mass per 100 parts by mass of the binder resin of the toner. When used as the internal additive, on the other hand, the charge control agent is used in an amount of 0.1 to 10 parts by mass and, specifically, 0.2 to 5 parts by mass per 100 parts by mass of the binder resin.

Further, the toners can be roughly grouped into pulverized toners obtained by the pulverization method and polymerized toners obtained by the polymerization method. It is, however, desired that the charge control agent is adjusted to assume a suitable degree of particle size irrespective of for which group of the toner the charge control agent of the invention is used.

When used for the pulverized toner, for example, it is desired that the charge control agent is used with its volume average particle diameter being adjusted to lie in a range of 0.1 to 20 μm and, specifically, 0.1 to 10 μm. If the volume average particle diameter is smaller than 0.1 μm, the charge control agent emerges in very small amounts on the surfaces of the toner, and the desired effect of charge control is not obtained. If the volume average particle diameter is larger than 20 μm, on the other hand, the charge control agent splits away in increased amounts from the toner causing such undesirable and adverse effect as contamination on the image-forming apparatus such as copying machine and the like.

When used for the polymerized toner, further, it is desired that the charge control agent is used with its volume average particle diameter being adjusted to lie in a range of not more than 1.0 μm and, specifically, from 0.01 to 1.0 μm. If the volume average particle diameter exceeds 1.0 μm, the toner for electrophotography that is finally obtained possesses a broad particle diameter profile, and tends to easily scatter causing fluctuation in the properties such as frictional charging property. If the charge control agent has an average particle diameter lying within the above range, on the other hand, the particle diameter profile of the toner can be sharpened, the charge control agent can be favorably dispersed in the toner, and the charge control agent is suppressed from being unevenly distributed among the toner particles eliminating fluctuation in the properties such as in the frictional charging property.

Further, the charge control agent of the present invention can be used in combination with any other known charge control agent having the negatively charging property.

As the other charge control agent having the negatively charging property, there can be exemplified an azo iron complex or a complex salt thereof, an azo chromium complex or a complex salt thereof, an azo manganese complex or a complex salt thereof, an azo cobalt complex or a complex salt thereof, an azo zirconium complex or a complex salt thereof, a chromium complex of carboxylic acid derivative or a complex salt thereof, a zinc complex of carboxylic acid derivative or a complex salt thereof, an aluminum complex of carboxylic acid derivative or a complex salt thereof, and a zirconium complex of carboxylic acid derivative or a complex salt thereof. The carboxylic acid derivative is, preferably, an aromatic hydroxycarboxylic acid and, specifically, a 3,5-di-tert-butylsalicylic acid.

In addition to the above, there can be exemplified a boron complex or a complex salt thereof, and a resin type charge control agent having the negatively charging property.

When the above other charge control agent is to be used in combination, the other charge control agent is added in an amount of, desirably, not more than 10 parts by mass per 100 parts by mass of the binder resin.

Upon using the charge control agent of the present invention for the coating material for applying, for example, an electrostatic powder, there can be formed a thick coating without defect. However, the charge control agent of the invention can be most effectively used being added to the toner that is used for forming images by the electrophotography.

<Toner>

The toner blended with the above charge control agent of the invention is used for forming images by the known electrophotography.

Except that the charge control agent of the invention is added thereto, the toner comprises chiefly a known binder resin. Further, the toner contains a coloring agent as well as various blending agents for toner The toner contains the charge control agent of the invention in the above-mentioned amount.

1. Binder Resins:

As the binder resins, there have been known vinyl resin, polyester resin, polyol resin, phenol resin, silicone resin, polyurethane resin, polyamide resin, furane resin, epoxy resin, xylene resin, terpene resin, cumaroindene resin, polycarbonate resin and petroleum resin. Usually, however, vinyl resin and polyester resin are preferably used.

The vinyl resin is obtained by polymerizing or copolymerizing a styrene monomer such as styrene or styrene derivative (e.g., α-methylstyrene, etc.), or a (meth)acrylic monomer such as (meth)acrylic acid or (meth)acrylic acid ester. Representative examples of the vinyl resin include a styrene resin which is a polymer of the styrene monomer, a (meth)acrylic resin which is a polymer of the (meth)acrylic monomer, and a styrene-(meth)acrylic copolymer resin which is a copolymer of the styrene monomer and the (meth)acrylic monomer.

The above vinyl resin is obtained by radically polymerizing the above monomer by using a polymerization initiator such as azobisisobutylonitrile or methyl ethyl ketone peroxide. Here, the above monomer can be copolymerized to some extent with a monomer having an ethylenically unsaturated group, such as olefin. It is further allowable to introduce a crosslinked structure into the vinyl resin by using, as the crosslinking agent, an aromatic divinyl compound such as divinylbenzene or a polyfunctional (meth)acrylic compound having a plurality of (meth)acryloyl groups, such as pentaerythritol triacrylate. By the copolymerization or by introducing the crosslinked structure, it is allowed to adjust the fixing property and offset property of the toner.

Among the vinyl resins, the styrene-(meth)acrylate copolymer resin is preferred and, specifically, a resin is preferred having at least one peak in a molecular weight region of 3,000 to 50,000 (calculated as number average molecular weight) and at least one peak in a molecular weight region of not less than 100,000 in the molecular weight distribution as measured for the tetrahydrofuran (THF)-soluble component by the gel permeation chromatography (GPC) from the standpoint of fixing property, offset property and preservability. It is further desired that the THF-soluble component of the vinyl resin has a molecular weight distribution in which 50 to 90% thereof has molecular weight of not more than 100,000, and most desirably has a main peak in the molecular weight region of from 5,000 to 30,000 (specifically, from 5,000 to 20,000).

Further, the vinyl polymer has an acid value in a range of 0.1 to 100 mgKOH/g, more preferably, 0.1 to 70 mgKOH/g and, most preferably, 0.1 to 50 mgKOH/g.

The acid value is measured in compliance with the JIS K-0070.

The polyester resin that is preferably used as a binder resin is obtained by the polycondensation reaction of a diol component such as ethylene glycol and a dicarboxylic acid such as phthalic acid.

Into the polyester resin, too, a crosslinked structure can be introduced by using an alcohol having a valency of three or more, such as sorbitol as the crosslinking agent. By introducing the crosslinked structure, it is allowed to adjust the properties of the toner such as fixing property and offset property.

It is desired that the polyester resin has at least one molecular weight peak in the molecular weight region of from 3,000 to 50,000 (calculated as number average molecular weight) in the molecular weight distribution measured for the THF-soluble component by the GPO from the standpoint of fixing property and offset resistance. It is further desired that the THF-soluble component has a molecular weight distribution in which 60 to 100% thereof has molecular weight of not more than 100,000, and most desirably has a main peak in the molecular weight region of from 5,000 to 20,000.

The polyester resin has an acid value in a range of 0.1 to 100 mgKOH/g, more preferably, 0.1 to 70 mgKOH/g and, most preferably, 0.1 to 50 mgKOH/g.

It is, further, desired that the polyester resin has a hydroxyl value of not more than 30 mgKOH/g and, specifically, in a range of 10 to 25 mgKOH/g.

Further, the polyester resins in an amorphous form and in a crystalline form may be mixed together to adjust the properties. In this case, the polyester resins to be mixed together should be selected by taking their compatibility with each other into consideration.

It is desired that the above resin binder has been so adjusted for its properties that the glass transition temperature (Tg) lies in a range of 35 to 80° C. and, specifically, 40 to 75° C. from the standpoint of toner preservability. If Tg is lower than 35° C., the toner tends to be deteriorated in a high-temperature atmosphere and, besides, tends to be offset at the time of fixing. If Tg exceeds 80° C., on the other hand, the fixing property tends to decrease.

In the polymerized toner produced by the polymerization method, it is desired that the binder resin has a softening point in a range of 80 to 140° C. If the softening point of the binder resin is lower than 80° C., the image that is formed loses stability and, besides, the toner may lose preservation stability. If the softening point exceeds 140° C., on the other hand, the fixing property is often deteriorated at low temperatures.

2. Coloring Agents:

The above binder resin is blended with a known coloring agent and, therefore, the image that is formed expresses a color corresponding to the coloring agent. The coloring agent is, usually, used in an amount of 0.1 to 20 parts by mass per 100 parts by mass of the binder resin though it may vary depending upon the kind thereof.

As the coloring agent, there is used a pigment or a dye depending on a color required for the toner.

For the black toner, for example, use is made of black or blue dye or pigment particles (e.g., carbon black or Phthalocyanine Blue).

For the toner for producing colors, further, there can be used a Magenta type dye or pigment, a Cyan type dye or pigment and a yellow type dye or pigment as coloring agents for three primary colors for expressing full color. There can be, further, used orange pigment, violet pigment, green pigment and white pigment. These pigments and dyes have all been known.

3. Agents to be Added to the Toner:

As the agents to be added to the toner together with the charge control agent and the coloring agent, there are typically used a magnetic material, a wax and a fluidity-improving agent.

The magnetic material is represented by, for example, a magnetite or a ferrite and is used for imparting magnetic property to the toner. Namely, the magnetic material is added to the toner when the electrostatic image is to be developed by using only the toner without using magnetic carrier. The above magnetic material is, usually, added to the binder resin in the form of a powder having an average particle diameter of about 0.1 to about 2 μm and in an amount of 10 to 200 parts by mass per 100 parts by mass of the binder resin.

The magnetic material can be also used as a coloring agent.

The wax will representatively be an aliphatic hydrocarbon wax such as low-molecular polyolefin or paraffin wax, or an oxidized polyethylene wax, and is used for improving the offset resistance of the toner. The wax, desirably, has a melting point in a range of 50 to 140° C. and, specifically, 70 to 120° C. from the standpoint of attaining the fixing property and offset resistance maintaining good balance. If the melting point is too low, for example, the anti-blocking property decreases. If the melting point is too high, on the other hand, the offset resistance becomes unsatisfactory.

The wax is, usually, used in an amount of 0.2 to 20 parts by mass and, specifically, 0.5 to 10 parts by mass per 100 parts by mass of the binder resin.

Further, the above coloring agent, magnetic material and wax are so-called internal additives which are used being dispersed in the binder resin. The fluidity-improving agent, on the other hand, is an external additive which is added on the toner surfaces to improve the fluidity of the toner (so as to smoothly flow). As the fluidity-improving agent, there can be used various fine powders (e.g., those having an average particle diameter of about 0.001 to about 2 μm). Preferably used is a fine powdery silica and, specifically, a dry-type silica (fumed silica) produced by the gas phase oxidation of a silicon halogenide compound.

The fluidity-improving agent is used, usually, in an amount of about 0.03 to about 8 parts by mass per 100 parts by mass of the toner particles.

The toner for which the charge control agent of the invention is used can be further blended, in addition to the above-mentioned blending agents, with a variety of kinds of additives that have been known per se., such as organic additives like various kinds of metal soaps, fluorine type surfactant and dioctyl phthalate as well as inorganic fine powdery additives in order to protect the photosensitive material and carrier, to improve cleaning property, to adjust thermal, electrical and physical properties, to adjust resistivity, to adjust softening point and to improve fixing ratio. The inorganic fine powdery additive may include electric conductivity-imparting agents (tin oxide, zinc oxide, carbon black, antimony oxide, etc.), titanium oxide, aluminum oxide and alumina. As required, further, the inorganic fine powdery additive may be rendered to be hydrophobic.

It is further allowable to use, in small amounts, lubricating agents such as polytetrafluoroethylene, zinc stearate and vinylidene polyfluoride, polishing agents such as cesium oxide, silicon carbide and strontium titanate, anti-caking agent, as well as white fine particles and black fine particles of a polarity opposite to that of the toner particles as development-improving agents.

The above additives may have been treated for their surfaces with such a treating agent as silicone varnish, silicone oil or silane coupling agent from the standpoint of controlling the amount of electric charge.

4. Preparation of the Toner.

The charge control agent of the invention and other charge control agents used as required, may be used as external additives but are, usually, used as internal additives, i.e., are used being dispersed in the binder resin together with the above-mentioned coloring agents and other agents (internal additives) to be added to the toner.

As described earlier, the toner can be represented by the pulverized toner produced by the pulverization method and the polymerized toner produced by the polymerization method. The charge control agent of the present invention can be used for either the pulverized toner and the polymerized toner.

The pulverized toner is produced as described below. Namely, by using a mixer such as Henschel's mixer, super-mixer or ball mill, the binder resin that has been prepared in advance is mixed with a coloring agent, a charge control agent and other agents (internal additives) to be added to the toner to a sufficient degree. Then by using a kneader or a monoaxial or biaxial extruder, the obtained mixture is melt-kneaded, solidified by cooling, pulverized and is, thereafter, classified into the toner of a predetermined particle size to obtain the pulverized toner.

The pulverization is attained by conducting, for example, a coarse pulverization by using a crusher or a hammer mill and a fine pulverization by using a pulverizer such as jet mill or high-speed rotary mill. The classification is conducted until the predetermined particle size is attained by using a wind classifier, an elbow jet of the inertial classification type based, for example, on the Coanda effect, a microplex of the cyclone (centrifugal) classification type or a DS separator.

To apply the external additive such as fluidity-improving agent to the surfaces of the toner, the toner and the external additive may be stirred and mixed together by using a high-speed stirrer such as Henschel' s mixer, ball mill, Nauta mixer, V-type mixer, W-type mixer or super-mixer.

The thus obtained pulverized toner is so adjusted for its particle size that the average particle diameter is about 2 to about 15 μm and, specifically, about 3 to about 12 μm on the volume basis. If the particle diameter of the toner is too great, the resolution and sharpness of the obtained image tend to decrease. If the particle diameter thereof is too small, on the other hand, the fluidity decreases, the amount of electric charge may decrease and, besides, there arouse such problems as poor cleaning and scattering of toner.

Further, the polymerized toner is obtained as described below. Namely, by using a suitable dispersant and a surfactant, the monomer used for forming the above binder resin is emulsified or is suspended and dispersed in a predetermined solvent (usually, water) together with a polymerization initiator, crosslinking agent, coloring agent, charge control agent and other agents to be added to the toner to thereby prepare a dispersion solution of a polymerizable monomer composition. The polymerizable monomer composition is then emulsion-polymerized or suspension-polymerized at 40 to 90° C. while adjusting the liquid droplets thereof to suitable sizes to thereby obtain toner particles having desired particle diameters. The obtained toner particles are washed, filtered and dried. The toner particles after having been produced are suitably subjected to the treatment for externally adding the fluidity-improving agent and the like thereto in a manner as described above.

The solution in which the polymerizable monomer composition is dispersed can be prepared by using a mixing machine or a dispersing machine, such as homo-mixer, homogenizer, atomizer, micro-fluidizer, one-liquid fluid nozzle, gas-liquid fluid nozzle or electric emulsifier. Upon adjusting the rate of stirring, temperature and time, the liquid droplets of the polymerizable monomer composition can be set to assume desired sizes. The size of the liquid droplets corresponds to the size of the toner particles.

The thus obtained polymerized toner has a uniform particle shape as compared to the pulverized toner, has a high degree of circularity, has less dents and protuberances on the surfaces of the particles, and has a sharp particle size profile. Therefore, a preferred range of particle diameters is slightly different from that of the pulverized toner; i.e., the average particle diameter on, for example, the volume basis, is desirably in a range of 3 to 9 μm, specifically, 4 to 8.5 μm and, most desirably, 5 to 8 μm. If the particle diameter of the toner is too large, the resolution and vividness tend to become dull. If the particle size of the toner is too small, on the other hand, the fluidity decreases, the amount of the electric charge may decrease and, besides, there occur such problems as poor cleaning and scattering of toner.

If the emulsion polymerization is employed for the above polymerization method, the liquid droplets of the polymerizable monomer composition become considerably smaller than those of the case of the suspension polymerization and, therefore, the average particle diameter of the obtained toner particles may become considerably small. Therefore, after the polymer particles are formed by the emulsion polymerization, a polymerizable monomer is added to grow the polymer particles with the particles as nuclei (so-called seed polymerization) to adjust the particle size. The particle size can also be adjusted by integrating or melt-adhering the particles obtained by the emulsion polymerization until a desired average particle diameter is attained.

The polymerized toner obtained by the polymerization method is not passing through the step of pulverization. Therefore, there is no need of imparting brittleness to the toner particles. Besides, the polymerized toner makes it possible to use in large amounts the low-softening materials that could not be used for the conventional toners obtained by the pulverization method, making it possible to select the materials from a wide range of materials. Moreover, the polymerized toner gives such advantages that a parting agent (wax) which is a hydrophobic material and a coloring agent are exposed little on the surfaces of the toner particles and, therefore, that the toner-carrier members, photosensitive material, transfer roller and fixing device are little contaminated.

The polymerized toner, on the other hand, was accompanied by a problem in that the charge control agent was heated in a state of being present together with water and, therefore, the electric charge could not be imparted to a sufficient degree. On the other hand, the charge control agent of the invention is capable of stably and excellently imparting the electric charge despite the environmental conditions are varied. Therefore, the toner blended with the charge control agent of the present invention excellently exhibits charging power irrespective of if the toner is the pulverized toner or the polymerized toner. That is, the toner is quickly charged by friction at a high rate, i.e., features a quick rise of charge, and a large amount of electric charge is stably maintained for extended periods of time. Specifically, the polymerized toner, too, exhibits such a large charging power that accounts for a great advantage of the charge control agent of the present invention.

Moreover, the charge control agent of the invention is colorless or lightly colored and does not hinder the hue even when it is added to a colored toner.

<Developing>

The toner blended with the charge control agent of the invention is used as a one-component developing agent or a two-component developing agent. By using the developing agent, an electrostatic latent image formed on the surface of the photosensitive material is visualized to form a toner image.

The one-component developing agent uses only the toner as the developing agent. The toner is fed onto the surface of a toner conveyer member such as developing roller, and a thin film of the toner that is electrically charged by friction is formed on the conveyer member. The thin film of the toner is fed, through a thickness-limiting member, to a developing zone where the electrostatic latent image formed on the photosensitive material (electrostatic image carrier) is developed. Usually, the toner (magnetic toner) blended with a magnetic material is used as the one-component developing agent.

The two-component developing agent, on the other hand, is a developing agent comprising the toner and a magnetic carrier. The toner is electrically charged (negatively in this invention) by friction of when the magnetic carrier and the toner are mixed and stirred together. The mixture (developing agent) of the two is fed onto a developing roller equipped with a magnet to form a magnetic brush of the developing agent on the developing roller. The magnetic brush having a predetermined ear length is fed, through an ear-cutting member, to a developing zone where the electrostatic latent image formed on the photosensitive material (electrostatic image carrier) is developed. Usually, the toner (nonmagnetic toner) without blended with the magnetic material is used for the two-component developing agent.

A particulate magnetic material such as of magnetite or ferrite is used as a magnetic carrier for the two-component developing agent. The toner is used, usually, in an amount of 1 to 200 parts by mass and, specifically, 2 to 100 parts by mass per 100 parts by mass of the magnetic carrier.

To prevent the toner from melt-adhering on the surfaces of the magnetic carrier, the magnetic carrier is often coated on its surfaces with a fluorine-contained resin or a silicone resin.

When the developing is to be conducted by using either the one-component developing agent or the two-component developing agent, too, the developing agent (toner) may or may not be in contact with the electrostatic latent image so far as an electric force is maintained for depositing the toner on the surfaces of the photosensitive material.

In conducting the developing with the developing agent not in contact with the electrostatic latent image, a predetermined DC electric field is applied between the developing roller and the photosensitive material and, besides, an alternating current is often superposed on the DC electric field so that the toner flies onto the surface of the photosensitive material.

The toner image formed on the surface of the photosensitive material by the above developing is transferred onto a sheet of paper or plastic material. The sheet on which the toner image is transferred is introduced into a fixing device where the toner image is fixed on the sheet by heat and pressure.

From the photosensitive material on which the toner image has been transferred, on the other hand, the toner that is remaining thereon is removed by using a cleaning blade. Thereafter, the electric charge is removed therefrom by the irradiation with light. Thus, a cycle of forming the image is completed. In the next cycle of forming the image, the whole surface of the photosensitive material is electrically charged (main charging), and is irradiated with light to form an electrostatic latent image (exposure to image-bearing light). The surface of the photosensitive material is next moved to move the electrostatic latent image to the developing zone where the developing, transfer and fixing are conducted in the same manner as described above. Further, the remaining toner is removed from the surface of the photosensitive material and the electric charge is removed therefrom, too.

EXAMPLES

The invention will now be described by way of Examples which, however, are in no way to limit the invention. In Examples, "parts" are all "parts by mass".

In the following experiments, the synthesized barbituric acid derivatives were refined by the column chromatography, by the adsorption by using silica gel, active carbon or active clay, by the recrystallization by using a solvent or by the crystallization method.

Further, the compounds were identified by the NMR analysis.

Synthesis Example 1

Synthesis of an Example Compound No. 1

Into a reaction vessel purged with nitrogen, there were added:
4-tert-butylbenzaldehyde, 6.5 g
1,3-dimethylbarbituric acid, 6.3 g
ethanol, 25 ml
water, 25 ml.

The mixture was heated and refluxed for 30 minutes with stirring. After cooled down to room temperature, the precipitated crystals were gathered by filtration and were, thereafter, dipped in and washed with ethanol to obtain 11.4 g of light cream-colored crystals of a 5-(4-tert-butylbenzilidene)-1,3-dimethylbarbituric acid (Example Compound No. 1) (yield, 95%).

The obtained light cream-colored crystals were identified for their structure relying on the NMR. The results of $^1$H-NMR measurement were as shown in FIG. 1.

The following twenty signals of hydrogen were detected by the $^1$H-NMR (DMSO-$d_6$).

δ (ppm)=8.33 (1H)
8.07-8.03 (2H)
7.52-7.48 (2H)
3.20 (6H)
1.32 (9H)

Synthesis Example 2

Synthesis of an Example Compound No. 2

Into the reaction vessel purged with nitrogen, there were added:
4-isopropylbenzaldehyde, 7.4 g
1,3-dimethylbarbituric acid, 7.8 g
ethanol, 30 ml
water, 30 ml.

The mixture was heated and refluxed for 3 hours with stirring. After cooled down to room temperature, the precipitated crystals were gathered by filtration and were, thereafter, dipped in and washed with ethanol to obtain 13.2 g of light yellow-colored crystals of a 5-(4-isopropylbenzilidene)-1,3-dimethylbarbituric acid (Example Compound No. 2) (yield, 92%).

Figure 2:
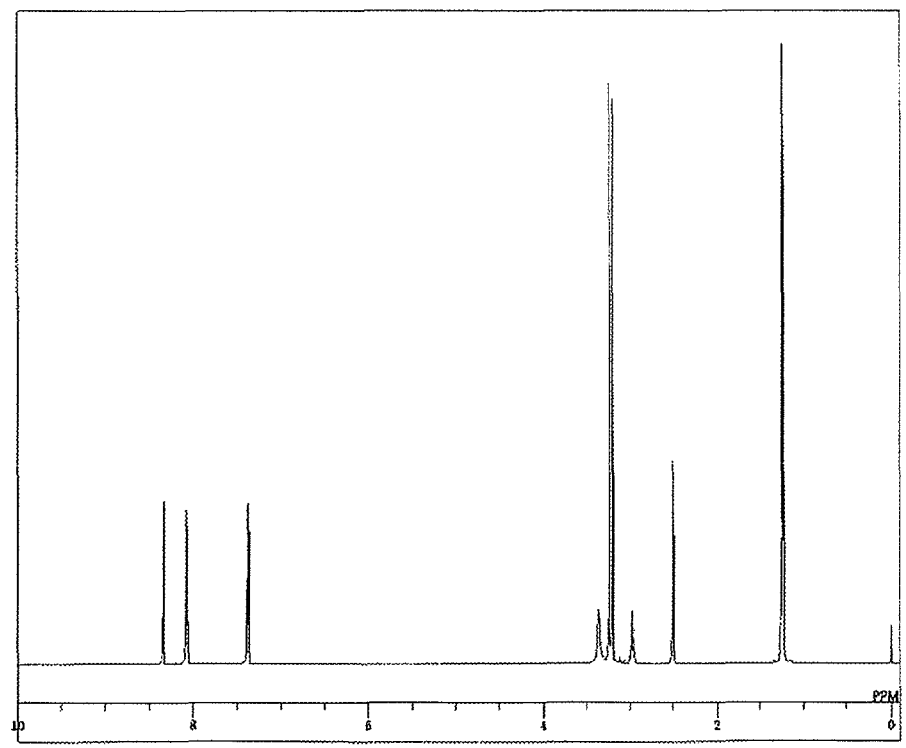
FIG. 2 is a 1H-NMR chart of a compound (Example compound No. 2) according to Example 2 of the present invention.

The obtained light yellow-colored crystals were identified for their structure relying on the NMR. The results of $^1$H-NMR measurement were as shown in FIG. 2.

The following eighteen signals of hydrogen were detected by the $^1$H-NMR (DMSO-$d_6$).
δ (ppm)=8.33(1H)
8.07-8.03 (2H)
7.40-7.36 (2H)
3.23 (3H)
3.20 (3H)
2.50 (1H)
1.24 (3H)
1.23 (3H)

Synthesis Example 3

Synthesis of an Example Compound No. 3

Into the reaction vessel purged with nitrogen, there were added:
4-(trifluoromethyl)benzaldehyde, 7.0 g
1,3-dimethylbarbituric acid, 6.3 g
ethanol, 25 ml
water, 25 ml.

The mixture was heated and refluxed for 10 minutes with stirring. After cooled down to room temperature, the precipitated crystals were gathered by filtration and were, thereafter, dipped in and washed with ethanol to obtain 12.5 g of light cream-colored crystals of a 5-{(4-trifluoromethyl)benzilidene}-1,3-dimethylbarbituric acid (Example Compound No. 3) (yield, 100%).

The obtained light cream-colored crystals were identified for their structure relying on the NMR. The following eleven signals of hydrogen were detected by the $^1$H-NMR (DMSO-$d_6$).
δ (ppm)=8.40 (1H)
8.01-7.97 (2H)
7.81-7.77 (2H)
3.26 (3H)
3.17 (3H)

Synthesis Example 4

Synthesis of an Example Compound No. 4

Into the reaction vessel purged with nitrogen, there were added:
benzaldehyde, 4.0 ml
1,3-dimethylbarbituric acid, 6.3 g
ethanol, 25 ml
water, 25 ml.

The mixture was heated and refluxed for 10 minutes with stirring. After cooled down to room temperature, the precipitated crystals were gathered by filtration and were, thereafter, dipped in and washed with ethanol to obtain 9.0 g of light cream-colored crystals of a 5-benzilidene-1,3-dimethylbarbituric acid (Example Compound No. 4) (yield, 92%).

The obtained light cream-colored crystals were identified for their structure relying on the NMR. The following twelve signals of hydrogen were detected by the $^1$H-NMR (DMSO-$d_6$).
δ (ppm)=8.36 (1H)
8.05-8.01 (2H)
7.56-7.52 (1H)
7.50-7.46 (2H)
3.24 (3H)
3.18 (3H)

Synthesis Example 5

Synthesis of an Example Compound No. 28

Into the reaction vessel purged with nitrogen, there were added:
2-methylbenzaldehyde, 7.81 g
1,3-dimethylbarbituric acid, 6.01 g
ethanol, 30 ml
water, 30 ml.

The mixture was heated and refluxed for 7.5 hours with stirring. After cooled down to room temperature, the precipitated crystals were gathered by filtration and were, thereafter, dipped in and washed with ethanol to obtain 11.05 g of yellow crystals of a 5-(2-methylbenzilidene)-1,3-dimethylbarbituric acid (Example Compound No. 28) (yield, 85.64%).

The obtained yellow crystals were identified for their structure relying on the NMR. The following fourteen signals of hydrogen were detected by the $^1$H-NMR (DMSO-$d_6$).
δ (ppm)=8.48 (1H)
7.52-7.53 (1H)
7.33-7.35 (1H)
7.27-7.28 (1H)
7.19-7.21 (1H)
3.18 (3H)
3.22 (3H)
2.28 (3H)

Synthesis Example 6

Synthesis of an Example Compound No. 29

Into the reaction vessel purged with nitrogen, there were added:
2-methoxybenzaldehyde, 6.81 g
1,3-dimethylbarbituric acid, 7.81 g
ethanol, 30 ml
water, 30 ml.

The mixture was heated and refluxed for 4 hours with stirring. After cooled down to room temperature, the precipitated crystals were gathered by filtration and were, thereafter, dipped in and washed with ethanol to obtain 13.24 g of yellow crystals of a 5-(2-methoxybenzilidene)-1,3-dimethylbarbituric acid (Example Compound No. 29) (yield, 96.6%).

The obtained yellow crystals were identified for their structure relying on the NMR. The following fourteen signals of hydrogen were detected by the $^1$H-NMR (DMSO-$d_6$).
δ (ppm)=8.55 (1H)
7.94-7.95 (1H)
7.51-7.54 (1H)
7.11-7.12 (1H)
6.97-7.00 (1H)
3.88 (3H)
3.23 (3H)
3.16 (3H)

Synthesis Example 7

Synthesis of an Example Compound No. 30

Into the reaction vessel purged with nitrogen, there were added:
2,4-dichlorobenzaldehyde, 7.00 g
1,3-dimethylbarbituric acid, 6.25 g
ethanol, 30 ml
water, 30 ml.

The mixture was heated and refluxed for 5 hours with stirring. After cooled down to room temperature, the precipitated crystals were gathered by filtration and were, thereafter, dipped in and washed with ethanol to obtain 12.09 g of light yellow crystals of a 5-(2,4-dichlorobenzilidene)-1,3-dimethylbarbituric acid (Example Compound No. 30) (yield, 96.5%).

The obtained light yellow crystals were identified for their structure relying on the NMR. The following ten signals of hydrogen were detected by the $^1$H-NMR (DMSO-$d_6$).

δ (ppm)=8.31 (1H)
7.71-7.72 (2H)
7.47-7.48 (1H)
3.25 (3H)
3.14 (3H)

Synthesis Example 8

Synthesis of an Example Compound No. 31

Into the reaction vessel purged with nitrogen, there were added:
2,4-dichlorobenzaldehyde, 3.19 g
1,3-dicyclohexylbarbituric acid, 5.33 g
pyridine, 30 ml The mixture was heated and refluxed for 3 hours with stirring. After cooled down to room temperature, the solvent was distilled off by using an evaporator. The remaining oil was added with 50 ml of methanol and was irradiated with ultrasonic waves, and there precipitated crystals. The precipitated crystals were gathered by filtration; i.e., there were obtained 7.38 g of light yellow crystals of a 5-(2,4-dichlorobenzilidene)-1,3-dicyclohexylbarbituric acid (Example Compound No. 31) (yield, 90.2%).

The obtained light yellow crystals were identified for their structure relying on the NMR. The following twenty-six signals of hydrogen were detected by the $^1$H-NMR (DMSO-$d_6$).

δ (ppm)=8.24 (1H)
7.75 (1H)
7.66-7.67 (1H)
7.49-7.51 (1H)
4.43-4.60 (2H)
1.07-2.23 (20H)

Synthesis Example 9

(Synthesis of an Example Compound No. 32)

Into the reaction vessel purged with nitrogen, there were added:
2,4-dichlorobenzaldehyde, 3.50 g
1,3-diphenylbarbituric acid, 5.93 g
pyridine, 30 ml The mixture was heated and refluxed for one hour with stirring. After cooled down to room temperature, the precipitated crystals were gathered by filtration and were, thereafter, dipped in and washed with ethanol to obtain 6.44 g of yellow crystals of a 5-(2,4-dichlorobenzilidene)-1,3-diphenylbarbituric acid (Example Compound No. 32) (yield, 73.6%).

The obtained yellow crystals were identified for their structure relying on the NMR. The following fourteen signals of hydrogen were detected by the $^1$H-NMR (DMSO-$d_6$).

δ (ppm)=8.42 (1H)
7.76-7.77 (2H)
7.33-7.52 (11H)

Example 10

Preparation of a Nonmagnetic Toner 1

| | |
|---|---|
| Styrene-acrylate copolymer resin, Trade name, CPR-100, manufactured by Mitsui Chemicals, Inc. Acid value: 0.1 mgKOH/g | 91 parts |
| Barbituric acid derivative synthesized in Synthesis Example 1 (Example Compound No. 1), | 1 part |
| Carbon black, Trade name, MA-100, manufactured by Mitsubishi Chemical Corporation. | 5 parts |
| Low-molecular polypropylene, Trade name, Viscol 550P, manufactured by Sanyo Chemical Industries, Ltd,. | 3 parts |
| were melted and mixed together by using a mixer (biaxial extrusion kneader) heated at 130° C. | |

The mixture was cooled, coarsely pulverized by a hammer mill, was, thereafter, finely pulverized by a jet mill and was classified to obtain a nonmagnetic toner 1 (pulverized toner) having a volume average particle diameter of 9±0.5 μm.

(Evaluation of the Nonmagnetic Toner 1)

The toner was mixed with an uncoated ferrite carrier (F-150 manufactured by Powder-Tech Co., Ltd.) (toner/carrier mass ratio=4/100), shaken to negatively charge, and was measured for its amount of electric charge by using a device for measuring the amount of electric charge of the blowoff powder. The results were as shown in Table 1.

The time constant (τ) which is an index of the rise of charging was calculated as described below.

The amount of electric charge was measured by using a device for measuring the charge amount of the blowoff powder for every predetermined period of time until the electric charge was saturated (see Electrophotography: The Society Journal, Vol. 27, No. 3, p. 307 (1988)), ln($q^{max}$-q) was calculated according to the following formula, and a relationship between the time t and ln ($q^{max}$-q) was plotted on a graph to find the time constant τ. The results were as shown in Table 1.

$$(q^{max}-q)/(q^{max}-q^0)=\exp(-t/\tau)$$

wherein $q^{max}$ is a saturated charge amount, $q^0$ is an initial charge amount (when the charging time is 10 seconds in this case), t is a measuring time, and q is an charge amount at that moment.

When the charge rises quickly, the time constant assumes a small value. The unit of the time constant is the second.

By using a ferrite carrier coated with silicon (F96-150 manufactured by Powder-Tech Co., Ltd.), further, the charge amount and the time constant were measured in quite the same manner as above. The results were as shown in Table 1.

Example 11

Preparation and Evaluation of a Nonmagnetic Toner 2

A nonmagnetic toner 2 was prepared by the same method as that of Example 10 but using a barbituric acid derivative (Example compound No. 2) synthesized in Synthesis Example 2 instead of using the barbituric acid derivative (Example compound No. 1). The charge amount and the time constant thereof were evaluated by using the device for measuring the charge amount of the blowoff powder.

The results were as shown in Table 1.

Example 12

Preparation and Evaluation of a Nonmagnetic Toner 3

A nonmagnetic toner 3 was prepared by the same method as that of Example 10 but using a barbituric acid derivative (Example compound No. 28) synthesized in Synthesis Example 5 instead of using the barbituric acid derivative (Example compound No. 1). The charge amount and the time constant thereof were evaluated by using the device for measuring the charge amount of the blowoff powder.

The results were as shown in Table 1.

Example 13

Preparation and Evaluation of a Nonmagnetic Toner 4

A nonmagnetic toner 4 was prepared by the same method as that of Example 10 but using a barbituric acid derivative (Example compound No. 29) synthesized in Synthesis Example 6 instead of using the barbituric acid derivative (Example compound No. 1). The charge amount and the time constant thereof were evaluated by using the device for measuring the charge amount of the blowoff powder.

The results were as shown in Table 1.

Example 14

Preparation and Evaluation of a Nonmagnetic Toner 5

A nonmagnetic toner 5 was prepared by the same method as that of Example 10 but using a barbituric acid derivative (Example compound No. 30) synthesized in Synthesis Example 7 instead of using the barbituric acid derivative (Example compound No. 1). The charge amount and the time constant thereof were evaluated by using the device for measuring the charge amount of the blowoff powder.

The results were as shown in Table 1.

Example 15

Preparation and Evaluation of a Nonmagnetic Toner 6

A nonmagnetic toner 6 was prepared by the same method as that of Example 10 but using a barbituric acid derivative (Example compound No. 31) synthesized in Synthesis Example 8 instead of using the barbituric acid derivative (Example compound No. 1). The charge amount and the time constant thereof were evaluated by using the device for measuring the charge amount of the blowoff powder.

The results were as shown in Table 1.

Example 16

Preparation and Evaluation of a Nonmagnetic Toner 7

A nonmagnetic toner 7 was prepared by the same method as that of Example 10 but using a barbituric acid derivative (Example compound No. 32) synthesized in Synthesis Example 9 instead of using the barbituric acid derivative (Example compound No. 1). The charge amount and the time constant thereof were evaluated by using the device for measuring the charge amount of the blowoff powder.

The results were as shown in Table 1.

Comparative Example 1

Preparation and Evaluation of a Comparative Nonmagnetic Toner

For comparison, a comparative nonmagnetic toner was prepared by the same method as that of Example 10 but using a salt of a 3,5-tert-butylsalicylic acid and a zinc instead of using the barbituric acid derivative (Example compound No. 1) synthesized in Synthesis Example 1. The charge amount and the time constant thereof were evaluated by using the device for measuring the charge amount of the blowoff powder.

The results were as shown in Table 1.

TABLE 1

|  | Carrier F-150 | | Carrier F96-150 | |
| --- | --- | --- | --- | --- |
| Toner | *1 | *2 | *1 | *2 |
| Example 10 | −29.8 | 115 | −26.5 | 102 |
| Example 11 | −28.2 | 118 | −26.4 | 104 |
| Example 12 | −27.4 | 121 | −26.1 | 106 |
| Example 13 | −27.7 | 119 | −25.4 | 103 |
| Example 14 | −28.3 | 123 | −24.7 | 103 |
| Example 15 | −29.6 | 108 | −26.7 | 101 |
| Example 16 | −28.1 | 116 | −25.8 | 105 |
| Comp. Ex. 1 | −23.0 | 200 | −15.0 | 108 |

*1: Charge amount (μc/g)
*2: Time constant τ (s)

As will be obvious from Table 1, the toners using a charge control agent that contains, as an effective component, a barbituric acid derivative represented by the general formula (1) of the invention, exhibit improved rise of charging and increased amounts of charge.

Example 17

Preparation of a Resin-Dispersed Solution

| | |
| --- | --- |
| Polyester resin, DIACRON ER-561, manufactured by Mitsubishi Rayon Co., Ltd. | 800 parts |
| Ethyl acetate, | 320 parts |
| Isopropyl alcohol, | 32 parts | were mixed together, and the mixture thereof was inverted for its phase and emulsified by adding a suitable amount of 0.1-mass % ammonia water thereto while stirring the mixture at 5,000 to 10,000 rpm by using a homogenizer (Bubble less Mixer NGM-0.5TB manufactured by BeRyu Co., Ltd.). Further, the solvent was removed therefrom while reducing the pressure by using the evaporator to obtain a resin-dispersed solution.

The volume average particle diameter of resin particles in the dispersion solution was 0.2 μm (concentration of the resin particles was adjusted with ion-exchanged water to be 20% by mass).

Preparation of a Charge Control Agent-Dispersed Solution

| | |
|---|---|
| Sodium dodecylbenzenesulfonate, | 0.2 parts |
| Solbon T-20 (manufactured by TOHO CHEMICAL INDUSTRY CO., LTD.), | 0.2 parts |
| Ion-exchanged water, | 17.6 parts |
| were mixed and dissolved together, and to which were further added, | |
| Barbituric acid derivative (Example compound No. 1) synthesized in Synthesis Example 1, | 2.0 parts, |
| Zirconia beads (particle diameter; 0.65 mmϕ, in an amount corresponding to 15 ml), | |
| and the mixture was dispersed for 3 hours by using a paint conditioner (UNION N.J. No. 5400-5 L manufactured by Red Devil, Inc, USA). The zirconia beads were removed by using a sieve, and there was obtained a solution in which 10% by mass of the charge control agent has been dispersed by being adjusted with ion-exchanged water). | |

Preparation of a Polymerized Toner

| | |
|---|---|
| Into a reaction vessel equipped with a thermometer, a pH meter and a stirrer, there were added: | |
| The above resin-dispersed solution, | 125 parts |
| An aqueous solution containing 20% by mass of sodium dodecylbenzenesulfonate, | 1.0 parts |
| Ion-exchanged water, | 125 parts |
| and the mixture thereof was stirred at a rotational speed of 150 rpm for 30 minutes while maintaining the liquid temperature at 30° C. An aqueous solution containing 1% by mass of nitric acid was added thereto to adjust the pH to be 3.0, and the mixture was stirred for another 5 minutes. While being dispersed by using a homogenizer (ULTRA-TURRAX T-25 manufactured by IKA Japan Co.), 0.125 parts of aluminum polychloride was added thereto, the liquid temperature was elevated up to 50° C., and the dispersion was continued for another 30 minutes. | |

Further, 62.5 parts of the above resin-dispersed solution and 4.0 parts of the charge control agent-dispersed solution were added thereto, and an aqueous solution containing 1% by mass of nitric acid was added thereto to adjust the pH to be 3.0. The dispersion was, further, continued for 30 minutes. 8.0 Parts of an aqueous solution containing 5% by mass of sodium hydroxide was added thereto while stirring the mixture at 400 to 700 rpm by using a stirrer, and the stirring was continued until the volume average particle diameter of the dispersed liquid droplets was 9.5 μm.

The liquid temperature was elevated to 75° C., and the mixture was stirred for another 2 hours. After it was confirmed that the volume average particle diameter was 6.0 μm and that the particles assumed a spherical shape, the mixture was quickly cooled with ice water. The toner was gathered by filtration, and was dispersed in and washed with the ion-exchanged water. The dispersion and washing were repeated until the electric conductivity of the filtrate after dispersion was not more than 20 μS/cm. Thereafter, the toner was dried by using a drier of 40° C. to obtain toner particles (polymerized toner).

The polymerized toner that was obtained was sieved by using a sieve of 166 mesh (perforation size of 90 μm) to use it as a toner for evaluation.

[Evaluation of the Toner]

2 Parts of the obtained toner for evaluation and 100 parts of the ferrite carrier coated with silicon (F96-150 manufactured by Powder-Tech Co., Ltd.) were mixed together and shaken to negatively charge the toner. Thereafter, the saturated amount of electric charge was measured by using the device for measuring the charge amount of the blowoff powder in an atmosphere of a temperature of 25° C. and a humidity of 50%.

As a result, the saturated amount of electric charge was −38.5 μC/g.

Example 18

A polymerized toner was prepared under the same conditions as those of Example 17 but using the barbituric acid derivative (Example compound No. 31) synthesized in Synthesis Example 8 instead of using the barbituric acid derivative (Example Compound No. 1), and the saturated charge amount thereof was measured. As a result, the saturated charge amount was −37.9 μC/g.

Comparative Example 2

For comparison, a toner was prepared under the same conditions as those of Example 17 but omitting the operation of adding the charge control agent-dispersion solution in Example 17, and the saturated charge amount thereof was measured. As a result, the saturated charge amount was −20.5 μC/g.

As will be obvious from the above results, it was learned that the polymer toner containing the barbituric acid derivative represented by the general formula (1) of the invention as an effective component, exhibited excellent electrically charging power.

Namely, by using the charge control agent containing the barbituric acid derivative represented by the general formula (1) of the invention as an effective component, it is allowed to impart a high electrically charging power to the polymerized toner.

INDUSTRIAL APPLICABILITY

The barbituric acid derivative represented by the general formula (1) of the invention has excellent electrically charging power, and the charge control agent containing the above compound as the effective component features obviously higher electrically charging power than that of the conventional charge control agents and excellent environmental stability. Further, the charge control agent is best suited for the colored toners and, specifically, for the polymerized toners. The invention, further, provides a very useful toner without containing heavy metals such as chromium compounds that are regarded to cause environmental problems.

The invention claimed is:

1. A charge control agent comprising a barbituric acid derivative represented by the following general formula (1), General formula (1):

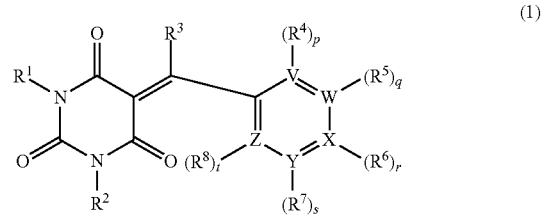

wherein, $R^1$ and $R^2$ may be the same or different, and are alkyl groups having 1 to 6 carbon atoms, cycloalkyl groups having 5 to 8 carbon atoms, aryl groups or heterocyclic groups, $R^3$ is a hydrogen atom, an alkyl group having 1 to 8 carbon atoms, a cycloalkyl group having 5 to 10 carbon atoms, an alkenyl group having 2 to 6 carbon atoms, an alkyloxy group having 1 to 8 carbon atoms, a cycloalkyloxy group having 5 to 10 carbon atoms, an aryloxy group, an aryl group or a hetrocyclic group, $R^4$ to $R^8$ may be the same or different, and are hydrogen atoms, deuterium atoms, fluorine atoms, chlorine atoms, bromine atoms, iodine atoms, hydroxyl groups, cyano groups, nitro groups, alkyl groups having 1 to 8 carbon atoms, cycloalkyl groups having 5 to 10 carbon atoms, alkenyl groups having 2 to 6 carbon atoms, alkyloxy groups having 1 to 8 carbon atoms, cycloalkyloxy groups having 5 to 10 carbon atoms, aryl groups, heterocyclic groups or aryloxy groups, and may be bonded to each other to form a ring and, further, $R^4$ may be bonded to $R^3$ to form a ring, V, W, X, Y and Z are carbon atoms or nitrogen atoms, and at least two of V, W, X, Y and Z are carbon atoms, p is a number of 0 or 1, and is 1 if V is a carbon atom and is 0 if V is a nitrogen atom, q is a number of 0 or 1, and is 1 if W is a carbon atom and is 0 if W is a nitrogen atom, r is a number of 0 or 1, and is 1 if X is a carbon atom and is 0 if X is a nitrogen atom, s is a number of 0 or 1, and is 1 if Y is a carbon atom and is 0 if Y is a nitrogen atom, and t is a number of 0 or 1, and is 1 if Z is a carbon atom and is 0 if Z is a nitrogen atom.

2. The charge control agent according to claim 1, wherein in the above general formula (1), $R^1$ and $R^2$ are alkyl groups having 1 to 4 carbon atoms but without substituent, cycloalkyl groups having 5 to 6 carbon atoms but without substituent, or substituted or unsubstituted aryl groups.

3. The charge control agent according to claim 1, wherein in the above general formula (1), $R^3$ is a hydrogen atom.

4. The charge control agent according to claim 1, wherein in the above general formula (1), V, W, X, Y and Z are all carbon atoms.

5. A toner containing the charge control agent of claim 1, a coloring agent and a binder resin.

6. The toner according to claim 5, wherein said charge control agent is dispersed in the binder resin in an amount of 0.1 to 10 parts by mass per 100 parts by mass of the binder resin, and the coloring agent is dispersed in the binder resin in an amount of 0.1 to 20 parts by mass per 100 parts by mass of the binder resin.

7. The toner according to claim 6, wherein the toner is obtained by a pulverization method or a polymerization method.

\* \* \* \* \*